United States Patent [19]

Shen

[11] Patent Number: 5,115,670
[45] Date of Patent: May 26, 1992

[54] MEASUREMENT OF FLUID PROPERTIES OF TWO-PHASE FLUIDS USING AN ULTRASONIC METER

[75] Inventor: Joseph Shen, Brea, Calif.

[73] Assignee: Chevron Research & Technology Company, San Francisco, Calif.

[21] Appl. No.: 490,864

[22] Filed: Mar. 9, 1990

[51] Int. Cl.$^5$ ............................................. G01N 29/02
[52] U.S. Cl. .................... 73/61.41; 73/861.29
[58] Field of Search ............ 73/61.1 R, 61 R, 861.04, 73/597, 53, 861.27, 861.28, 861.29

[56] References Cited

U.S. PATENT DOCUMENTS

| | | | |
|---|---|---|---|
| 4,080,837 | 3/1978 | Alexander et al. | 73/61.1 R |
| 4,135,387 | 1/1979 | Benedict | 73/53 |
| 4,581,942 | 4/1986 | Ogura et al. | 73/861.04 |
| 4,683,759 | 8/1987 | Skarsvaag et al. | 73/861.04 |
| 4,856,321 | 8/1989 | Smalling et al. | 73/40.5 A |

FOREIGN PATENT DOCUMENTS

3429361  2/1986  Fed. Rep. of Germany ..... 73/61 R

OTHER PUBLICATIONS

E. E. Michaelides et al, "Velocity of Sound in Two-Phase Mixtures" *Int. J. Heat & Fluid Flow*, vol. 4, No. 2, Jun. 1983, pp. 79-84.

*Primary Examiner*—Hezron E. Williams
*Assistant Examiner*—Joseph W. Roskos
*Attorney, Agent, or Firm*—E. J. Keeling; E. A. Schaal

[57] ABSTRACT

A method is disclosed for determining the composition of a two-phase fluid, such as saturated steam. In that method, the transit times of sound are measured within the two-phase fluid, the speed of sound of the two-phase fluid is calculated from the measured transit times, and the composition of the two-phase fluid is calculated from the calculated speed of sound. From the calculated linear velocity and the calculated composition, one can calculate at least one fluid property of the two-phase fluid, such as mass flow rate or energy flow rate. All of these calculations can be performed by a microprocessor.

10 Claims, 1 Drawing Sheet

MEASUREMENT OF FLUID PROPERTIES OF TWO-PHASE FLUIDS USING AN ULTRASONIC METER

The present invention relates to the measurement of fluid properties of two-phase fluids.

BACKGROUND OF THE INVENTION

Often, in the production of crude oil, steam needs to be injected into the petroleum reservoir because the crude oil is too viscous. Two parameters are usually required to describe a wet, saturated steam flow in a conduit—the total flow rate and the steam quality. The steam quality is defined as the mass fraction of the vapor phase in steam. Once the steam quality is known, properties such as specific volume and enthalpy can be calculated for a given saturation temperature or pressure.

In the current practice of steam metering, two measuring devices are usually needed to obtain the flow rate and steam quality. For example, U.S Pat. No. 4,753,106 by Brenner et al. discloses using an orifice meter to measure the flow rate and a densitometer to measure the density, hence to deduce the quality. U.S. Pat. No. 4,681,466 by Chien et al. discloses a method using two flow meters, but that method is sometimes less than successful because it is based on empirical correlations of flow measurements. U.S. Pat. No. 4,712,006 by Zemel et al. and U.S. Pat. No. 4,645,635 by Yuen et al. both disclose using radioactive elements to measure density, hence quality, but those methods are not easy to apply. Brenner et al., Chien et al., Zemel et al., and Yuen et al. are hereby incorporated by reference for all purposes.

SUMMARY OF THE INVENTION

The present invention is a method for determining the composition of a two-phase fluid, such as saturated steam, using only one meter. Since only one meter is used, this invention has advantages over the prior art, which usually require multiple devices.

The present invention involves measuring transit times of sound within the two-phase fluid, calculating the speed of sound of the two-phase fluid from the measured transit times, and calculating the composition of the two-phase fluid from the calculated speed of sound.

Fluid properties of a flowing two-phase fluid (such as mass flow rate and energy flow rate) can be determined by one embodiment of that invention. It involves measuring transit times of sound within the two-phase fluid, calculating both the speed of sound and the linear velocity of the two-phase fluid from the measured transit times, calculating the composition of the two-phase fluid from the calculated speed of sound, and calculating at least one fluid property of the two-phase fluid from the calculated linear velocity and the calculated composition. Preferably, the two-phase fluid is a homogeneous, saturated steam. All of those calculations can be performed by a microprocessor.

BRIEF DESCRIPTION OF THE DRAWINGS

In order to facilitate the understanding of this invention, reference will now be made to the appended drawings of the preferred embodiments of the present invention. The drawings are exemplary only, and should not be construed as limiting the invention.

DETAILED DESCRIPTION OF THE PREFERRED EMBODIMENTS

Figure 1:
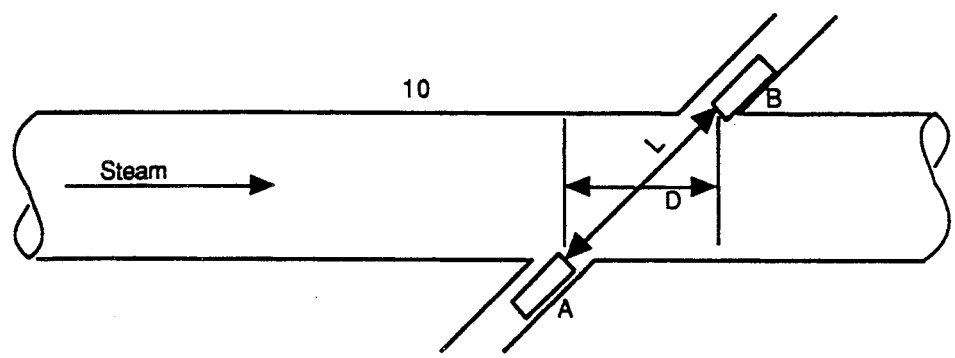
FIG. 1 is a schematic drawing of one embodiment of the present invention.

In its broadest aspect, the present invention uses only one meter to obtain the needed information, resulting in less equipment and simpler operation.

The composition of a two-phase fluid is determined by measuring transit times of sound within the two-phase fluid, calculating the speed of sound of the two-phase fluid from the measured transit times, and calculating the composition of the two-phase fluid from the calculated speed of sound.

In one embodiment, an ultrasonic meter, suitably adapted to be operated in a high temperature (465° F.) and high pressure (500 psia) environment, is installed in the steam line. The meter, with its electronic circuitry, measures a sonic velocity and bulk average velocity of the homogeneous wet steam flow using the transit-time principle.

One particular advantage of the present invention is its ability to measure concurrently two properties of a wet steam flow: sonic velocity and average bulk velocity. The sonic velocity, being a thermodynamic property of the wet steam, depends on another thermodynamic property, the steam quality. Once the quality is calculated from the sonic velocity, all other parameters can be calculated by knowing the bulk velocity and other properties found in the Steam Table.

The Two-Phase Fluid

By "two-phase fluid," we mean a fluid that exists in two phases concurrently. For example, water can exist both in the gaseous and liquid phase at 500° F. and 680 psia. The composition of the two-phase fluid (i.e., the fraction of each phase) at the saturation temperature and pressure can vary anywhere from 0 to 100% for one phase, with the balance in the other phase.

While the methods and apparatuses of this invention can be used to determine the composition of a variety of two-phase fluids, they work especially well for the determination of the composition of steam. Preferably, the steam is saturated steam. More preferably, it is a homogeneous, saturated steam.

The Measurement of Transit Times

The first step of the present invention involves determining the composition of a two-phase fluid by measuring transit times of sound within the two-phase fluid. By "transit time of sound" we mean the time for a sonic pulse to travel in the fluid medium between a pair of acoustic transducers. The pulses travel at the speed of sound that is characteristic of the two-phase fluid at the measured temperature. If the fluid medium is not stationary, the sonic speed of the pulses will be either aided or retarded by the linear velocity of the fluid, depending upon the direction of the pulses relative to the direction of fluid movement.

The transit times of sound can be measured using pairs of acoustic transducers that alternately act as transmitters and receivers in sending and receiving pulses. A typical frequency range of those pulses is from 50 kilo hertz to 1 million hertz.

A transit-time ultrasonic meter can measure two quantities when installed in a steam line: the average velocity, U, of the flow and the speed of sound, C, of the steam. From these two quantities, the flow rate, quality, and enthalpy of the steam stream can be deduced.

Referring to FIG. 1, acoustic transducers A and B are placed diagonally across steam line 10 as steam passes through the line. The distance L between the two transducers is known. Also known is the horizontal component D of that distance. The transit times between these transducers are measured in both directions.

The Calculation of Speed of Sound

In the next step, the speed of sound of the two-phase fluid is calculated from the measured transit times.

For a transit-time ultrasonic meter as set up in FIG. 1, U and C can be deduced by Equations 1 and 2:

$$U = \frac{L^2 (T_{BA} - T_{AB})}{2D\, T_{AB}\, T_{BA}} \tag{1}$$

$$C = \frac{L (T_{AB} + T_{BA})}{2\, T_{AB}\, T_{BA}} \tag{2}$$

where $T_{AB}$ and $T_{BA}$ are the transit times for the sonic pulses to travel between transducers A and B. L and D are known dimensions in the meter setup. The travel times can be measured by the electronics in commercial ultrasonic meters currently on the market.

The Calculation of Composition

Then, the composition of the two-phase fluid is calculated from the calculated speed of sound.

The quality, being a property of the steam at a saturation temperature or pressure, can be related to the speed of sound which is also a thermodynamic property of the steam. Michaelides and Zissis (1983) showed that the speed of sound of a homogeneous wet steam mixture can be calculated by Equation 3.

$$C^2 = \frac{[v_f(1 - x) + x v_g] \left[\dfrac{dP}{dT}\right]^2}{\dfrac{1}{T}\dfrac{dh_f}{dT} + x\, v_{fg}\dfrac{d^2P}{dT^2} - \dfrac{dP}{dT}\dfrac{dV_f}{dT}} \tag{3}$$

where, except the steam quality x, all terms such as the specific volume v, enthalpy h, and saturation pressure P in the right-hand side of Equation 3 are either known values of thermodynamic properties of the steam in the Steam Tables or obtainable by correlations of those properties as a function of the saturation temperature T. Subscripts f and g denote liquid and vapor phase, respectively. Equation 3 can then be re-written to solve for x as shown in Equation 4.

$$x = \frac{-J + \sqrt{J^2 - 4IK}}{2I} \tag{4}$$

where $$I = v_{fg}^2 \left(\frac{dP}{dT}\right)^2$$

$$J = 2\, v_f v_{fg} \left(\frac{dP}{dT}\right)^2 - v_{fg}\frac{d^2P}{dT^2} C^2$$

$$K = v_f^2 \left(\frac{dP}{dT}\right)^2 + \frac{dP}{dT}\,\frac{dv_f}{dT}\, C^2 - \frac{1}{T}\,\frac{dh_f}{dT}\, C^2$$

Thus, at a given saturation temperature T, all terms in Equation 4 involving P, v, and h are either known from the Steam Table or can be computed from correlations based on the saturation temperature T.

Figure 2:
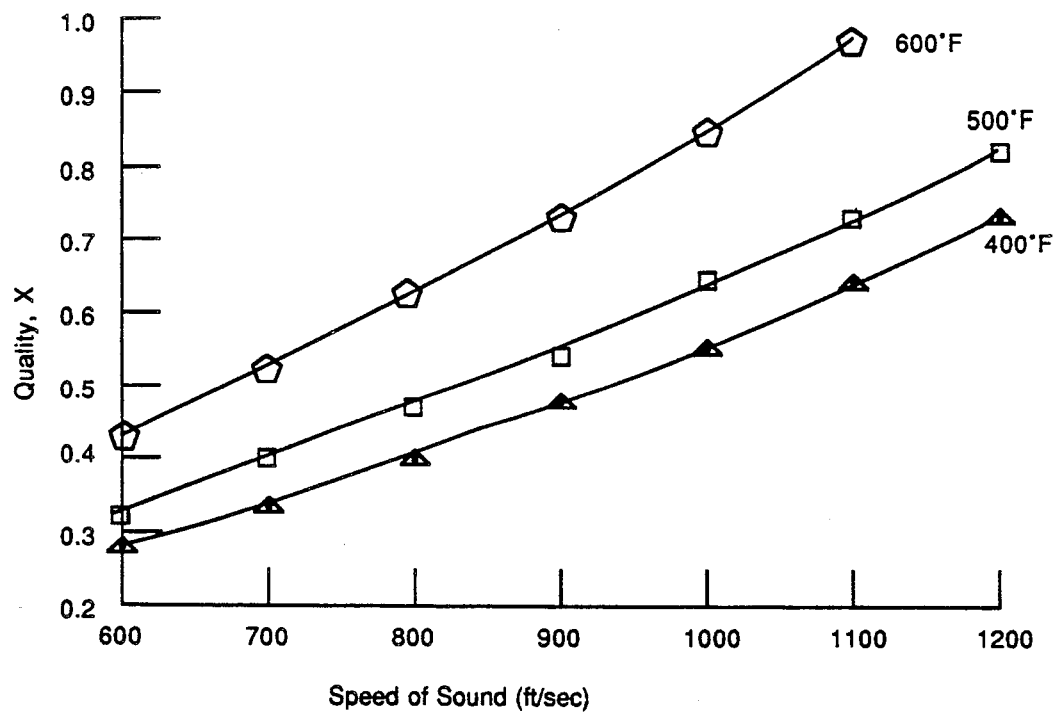
FIG. 2 is a plot of the quality of saturated steam versus speed of sound in ft/sec for various temperatures.

The quality, x, can be then calculated based on the measured speed of sound, C. Equation 4 is plotted in FIG. 2 where the quality, x, is shown as a function of the speed of sound measurement at various saturation temperature. Note that this scheme of computing steam quality based on the measured speed of sound is thermodynamically rigorous as compared to other acoustic schemes based on empiricism (e.g., U.S. Pat. No. 4,193,290 by Sustek, Jr. et al.)

The Calculation of Fluid Property

Once the quality is known, the enthalpy and any other thermodynamic properties of wet steam mixture can be calculated by the following formula:

$$h = h_f(1-x) + h_g x \tag{5}$$

For a homogeneous wet steam mixture, the flow rate, Q, is obtained simply by multiplying the measured average velocity and the cross sectional area, A, of the flowing tube as shown in Equation 6.

$$Q = U\, A \tag{6}$$

In one embodiment, at least one fluid property of a flowing two-phase fluid is determined by the four steps of:

(a) measuring transit times of sound within the two-phase fluid, (b) calculating both the speed of sound and the linear velocity of the two-phase fluid from the measured transit times, (c) calculating the composition of the two-phase fluid from the calculated speed of sound, and (d) calculating at least one fluid property of the two-phase fluid from the calculated linear velocity and the calculated composition.

Preferably, the fluid property that is determined is either mass flow rate or energy flow rate. All of these calculations can be performed by a microprocessor. The microprocessor can be a means for calculating both the speed of sound of the two-phase fluid from the measured transit times and the composition of the two-phase fluid from the calculated speed of sound.

In one embodiment, the microcomputer is a calculating means for calculating:

(1) the speed of sound and the linear velocity of the two-phase fluid from the measured transit times, (2) the composition of the two-phase fluid from the calculated speed of sound, and (3) at least one fluid property of the two-phase fluid from the calculated linear velocity and the calculated composition.

While the present invention has been described with reference to specific embodiments, this application is intended to cover those various changes and substitutions which may be made by those skilled in the art without departing from the spirit and scope of the appended claims.

What is claimed is:

1. A method for determining the composition of a flowing two-phase fluid that has a gaseous phase and a liquid phase comprising:
    (a) measuring transit times of sound within said two-phase fluid using a pair of acoustic transducers that alternately act as transmitters and receivers in sending and receiving pulses,
    (b) calculating the speed of sound of said two-phase fluid from said measured transit times, and
    (c) calculating the composition of said two-phase fluid from said calculated speed of sound.

2. A method according to claim 1 wherein said two-phase fluid is steam.

3. A method according to claim 2 wherein said steam is saturated steam.

4. A method for determining at least one fluid property of a flowing two-phase fluid comprising:
    (a) measuring transit times of sound within the two-phase fluid using a pair of acoustic transducers that alternately act as transmitters and receivers in sending and receiving pulses,
    (b) calculating both the speed of sound and the linear velocity of said two-phase fluid from said measured transit times,
    (c) calculating the composition of said two-phase fluid from said calculated speed of sound, and
    (d) calculating at least one fluid property of said two-phase fluid form said calculated linear velocity and said calculated composition.

5. A method according to claim 4 wherein said two-phase fluid is a homogeneous, saturated steam.

6. A method according to claim 4 wherein said fluid property is selected from the group consisting of mass flow rate and energy flow rate.

7. A method according to claim 4 wherein all of said calculations are performed by a microprocessor.

8. An apparatus for determining the composition of a two-phase fluid comprising:
    (a) a pair of acoustic transducers that alternately act as transmitters and receivers in sending and receiving pulses for measuring transit times of sound within the two-phase fluid, and
    (b) means for calculating both the speed of sound of said two-phase fluid from said measured transit times and the composition of said two-phase fluid from said calculated speed of sound.

9. An apparatus for determining at least one fluid property of a two-phase fluid comprising:
    (a) a pair of acoustic transducers that alternately act as transmitters and receivers in sending and receiving pulses for measuring the transit times of sound within the two-phase fluid, and
    (b) a calculating means for calculating:
        (2) the speed of sound the linear velocity of said two-phase fluid from said measured transit times,
        (2) the composition of said two-phase fluid from said calculated speed of sound, and
        (3) at least one fluid property of said two-phase fluid from said calculated linear velocity and said calculated composition.

10. An apparatus according to claim 9 wherein said calculating means is a microprocessor.

* * * * *